(12) United States Patent
Page et al.

(10) Patent No.: US 6,362,197 B1
(45) Date of Patent: Mar. 26, 2002

(54) COMPOSITIONS AND METHOD FOR TREATMENT OF COUGH

(75) Inventors: Clive P. Page, London (GB); Bernard A. MacLeod; David M. J. Quastel, both of British Columbia (CA)

(73) Assignee: Cardiome Pharma Corp. (CA)

( * ) Notice: Subject to any disclaimer, the term of this patent is extended or adjusted under 35 U.S.C. 154(b) by 0 days.

(21) Appl. No.: 09/328,540

(22) Filed: Jun. 9, 1999

Related U.S. Application Data

(60) Provisional application No. 60/088,597, filed on Jun. 9, 1998.

(51) Int. Cl.[7] .................................................. A61K 31/47
(52) U.S. Cl. ....................................... 514/312; 514/850
(58) Field of Search .................................. 514/312, 850

(56) References Cited

FOREIGN PATENT DOCUMENTS

GB             995256    *   6/1965   ................. 514/312

OTHER PUBLICATIONS

Caplus 100:114885, Lyttkens et al., Local anesthetics and tinnitus. Proposed peripheral mechanism of action of lidocaine, Journal for oto–rhino–laryngology and its borderlands. 46(1) see abstract, 1984.*

* cited by examiner

Primary Examiner—Frederick Krass
Assistant Examiner—Donna Jagoe
(74) Attorney, Agent, or Firm—Nields & Lemack

(57) ABSTRACT

Pharmaceutical compositions possessing anti-tussive activity, and a method of administering the same to warm-blooded animals, including humans.

2 Claims, 2 Drawing Sheets

COMPOSITIONS AND METHOD FOR TREATMENT OF COUGH

This application claim benefit to Provisional Application No. 60/088,597 filed Jun. 9, 1998.

BACKGROUND OF THE INVENTION

Conventional cough preparations containing an effective anti-tussive agent such as codeine have long been used for the symptomatic relief of coughs. However, codeine has various side effects which are undesirable.

Accordingly, the present invention relates to compositions of matter useful as pharmaceutical compositions having anti-tussive activity, and a method of treating warm-blooded animals affected by coughs or bronchoconstriction by administering an effective amount of the pharmaceutical compositions of the invention.

SUMMARY OF THE INVENTION

The problems of the prior art have been overcome by the present invention, which provides pharmaceutical compositions possessing anti-tussive activity, and a method of administering the same to warm-blooded animals, including humans. The active anti-tussive agent in accordance with the present invention is a quaternary ammonium compound represented by the following formula (I) and its pharmaceutically acceptable salts:

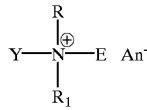

(I)

wherein Y and E are independently selected from —$CH_2$—$R_2$ or:

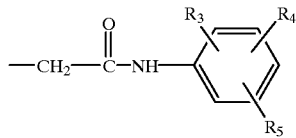

wherein R, $R_1$ and $R_2$ are independently selected from hydrogen, $C_1$–$C_8$ alkyl, $C_3$–$C_8$ alkoxyalkyl and $C_7$–$C_{12}$ aralkyl; and where $R_3$, $R_4$ and $R_5$ are independently selected from bromine, chlorine, fluorine, carboxy, hydrogen, hydroxy, hydroxymethyl, methanesulfonamido, nitro, sulfamyl, trifluoromethyl, $C_2$–$C_7$ alkanoyloxy, $C_1$–$C_6$ alkyl, $C_1$–$C_6$ alkoxy, $C_2$–$C_7$ alkoxycarbonyl, $C_1$–$C_6$ thioalkyl, aryl and N($R_6$, $R_7$) where $R_6$ and $R_7$ are independently selected from hydrogen, acetyl, methanesulfonyl and $C_1$–$C_6$ alkyl, $An^{31}$ is the acid addition salt of a pharmaceutically acceptable acid or the anion from a pharmaceutically acceptable salt, and isolated enantiomeric, diastereomeric and geometric isomers thereof, and mixtures thereof, with the proviso that Y and E cannot both be —$CH_2$—$R_2$ in the same compound.

DETAILED DESCRIPTION OF THE INVENTION

Figure 1:
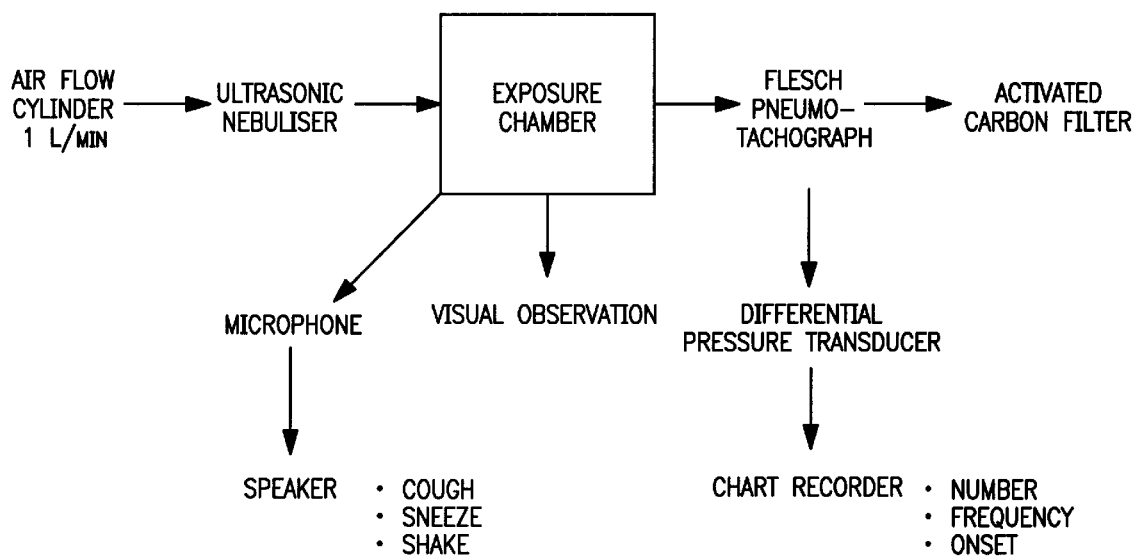
FIG. 1 is a flow diagram showing the layout of the experimental apparatus used for cough determination.

As used herein, the following terms have the following meaning:

"Alkyl" refers to a branched or unbranched hydrocarbon fragment containing the specified number of carbon atoms and having one point of attachment. Examples include n-propyl (a $C_3$ alkyl), isopropyl (also a $C_3$ alkyl) and t-butyl (a $C_4$ alkyl).

"Alkoxyalkyl" refers to an alkylene group substituted with an alkoxy group. For example, methyoxyethyl ($CH_3OCH_2CH_2$—) and ethoxymethyl ($CH_3CH_2OCH_2$—) are both $C_3$ alkoxyalkyl groups.

"Alkylene" refers to a divalent radical which is a branched or unbranched hydrocarbon fragment containing the specified number of carbon atoms and having two points of attachment. An example is propylene (—$CH_2CH_2CH_2$—), a $C_3$ alkylene.

"Aralkyl" refers to an alkylene group wherein one of the points of attachment is to an aryl group. An example is the benzyl group ($C_6H_5CH_2$—), a $C_7$ aralkyl group.

"Alkanoyloxy" refers to an ester substituent wherein the ether oxygen is the point of attachment to the molecule. Examples include propanoyloxy ($CH_3CH_2C(O)O$—), a $C_3$ alkanoyloxy and ethanoyloxy ($CH_3C(O)O$—), a $C_2$ alkanoyloxy.

"Alkoxy" refers to an O-atom substituted by an alkyl group, for example methoxy (—$OCH_3$), a $C_1$ alkoxy.

"Alkoxycarbonyl" refers to an ester substituent wherein the carbonyl carbon is the point of attachment to the molecule. Examples include ethoxycarbonyl ($CH_3CH_2OC=O$), a $C_3$ alkoxycarbonyl, and methoxycarbonyl ($CH_3OC(O)$—), a $C_2$ alkoxycarbonyl.

"Aryl" refers to aromatic groups which have at least one ring having a conjugated pi electron system and includes carbocyclic aryl, heterocyclic aryl (also known as heteroaryl groups) and biaryl groups, all of which may be optionally substituted. Carbocyclic aryl groups are generally preferred in the compounds of the present invention, wherein phenyl and naphthyl groups are preferred carbocyclic aryl groups.

"Cycloalkyl" refers to a ring, which may be saturated or unsaturated and monocyclic, bicyclic or tricyclic formed entirely from carbon atoms. An example is the cyclopentenyl group ($C_5H_7$—), which is a five carbon unsaturated cycloalkyl group.

"Carbocyclic" refers to a ring which may be either an aryl ring or a cycloalkyl ring, both as defined above.

"Thioalkyl" refers to a sulfur atom substituted by an alkyl group, for example thiomethyl ($CH_3S$—), a $C_1$ thioalkyl.

The origin of the cough to be treated by the present invention is not particularly limited, and can include virtually any respiratory disorder, such as chronic obstructive pulmonary disease, tuberculosis, bronchitis, respiratory malignancies, asthma, allergy, pulmonary fibrosis, respiratory tract inflammation, emphysema, pneumonia, lung cancer, presence of foreign bodies, soar throat, common cold, influenza, respiratory tract infection, bronchoconstriction, inhalation of irritants, smoker's cough, chronic non-productive cough, neoplastic cough, cough due to angiotension converting enzyme (ACE) inhibitor therapy, etc.

The preferred compound of the present invention is a compound of the formula (I) wherein R and $R_1$ are methyl and Y and E are each

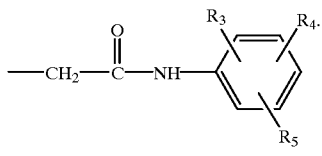

This compound, where $R_3$, $R_4$ and $R_5$ are each hydrogen ("Compound 1"), was synthesized as described in Belgium Patent No. 614,154, which follows from Swedish Patent 1779/61, the disclosures of which are herein incorporated by reference. A conventional route of synthesis involves three steps and can be described (as in the aforementioned patent; see also T. Takahashi, J. Okada, M. Hori, A. Kato, K. Kanematsu, and Y. Yamamoto, *J. Pharm. Soc. Japan* 76, 1180–6 (1956)) as follows:

i) Chloroacetanilide

To a chilled solution of aniline (37.2 g, 0.40 mol) and potassium carbonate (66.4 g, 0.48 mol) in chloroform (200 ml) was added dropwise via cannula a solution of chloro-acetylchloride (49.6 g, 0.44 mol) in chloroform (100 ml) and the reaction mixture was heated to 55° C. for 90 min. To the cooled reaction mixture was then added water (300 ml), the organic layer was collected and the aqueous layer was extracted twice more with chloroform (2×100 ml). The combined organic layers were dried over sodium sulfate and evaporation of the solvent in vacuo provided the crude product. The product was purified via extraction through a Soxhlet apparatus with diethyl ether to provide 22. g of the desired chloroacetanilide. m.p. 133–135° C., $^1$H NMR (CDCl$_3$, 200 MHz) δ: 8.3 (br. s, NH, 1H), 7.6–7.1 (m, Ar, 5H) 4.1 (s, CH$_2$, 2H).

ii) Dimethylaminoacetanilide

A mixture of chloroacetanilide (10.0 g, 59 mmol) in dimethylamine, 40% wt in water (100 ml) was refluxed for 4 hours. The cooled reaction mixture was partitioned between dichloromethane (100 ml) and 1M NaOH aqueous solution (100 ml). The aqueous layer was extracted twice more with dichloromethane (2×100 ml), the combined organic layers were concentrated in vacuo to a volume of approximately 100 ml and washed with water (2×100 ml) in order to remove the remaining dimethylamine. The organic layer was collected, dried over sodium sulfate and the solvent evaporated in vacuo to provide 10.2 g (97% yield) of the pure dimethylaminoacetanilide. $^1$H NMR (CDCl$_3$, 200 MHz) δ: 9.1 (br. s, NH, 1H), 7.6–7.0 (m, Ar, 5H) 3.1 (s, CH$_2$, 2H), 2.4 (s CH$_3$, 6H).

iii) N,N-Bis-(phenylcarbamoylmethyl)dimethylammonium chloride

A mixture of chloroacetanilide (10.1 g, 59.5 mmol), dimethylaminoacetanilide (10.7 g, 60 mmol) and potassium iodide, 99+% (0.1 g, 0.6 mmol) in dry xylene (30 ml) was refluxed for 1 hour and then allowed to stand overnight to ambient temperature. The solvent was decanted and the remaining gummy solid was triturated in diethyl ether in order to obtain a whitish powder. The resulting solid was collected and recrystallized in a mixture of ethanol and diethyl ether to provide 9.3 g (45% yield) of the desired ammonium salt. m.p. 177–178° C., $^1$H NMR (DMSO-d$_6$, 300 MHz) δ:11.3 (s, NH, 2H), 7.7–7.1 (m, Ar, 10 H) 4.8 (s, CH$_2$, 4H), 3.6 (s CH$_3$, 6H), $^{13}$C NMR (DMSO-d$_6$, 75 MHz) δ:162.1(+), 137.8 (+), 128.8 (–), 124.3 (–), 119.7 (–), 63.0 (+), 52.8 (–), LRMS(EI) m/z=297 (0.95%, M$^+$—CH3), elemental analysis calculated for C$_{18}$H$_{22}$N$_4$O$_2$Cl (347.84): C, 62.15; H, 6.37; N, 12.08; found: C, 61.75; H, 6.50; N, 12.04.

Reference: A. P. Truant and J. R. Dahlbom Belguim Patent No. 614154, Feb. 20, 1961.

Synthetic Scheme

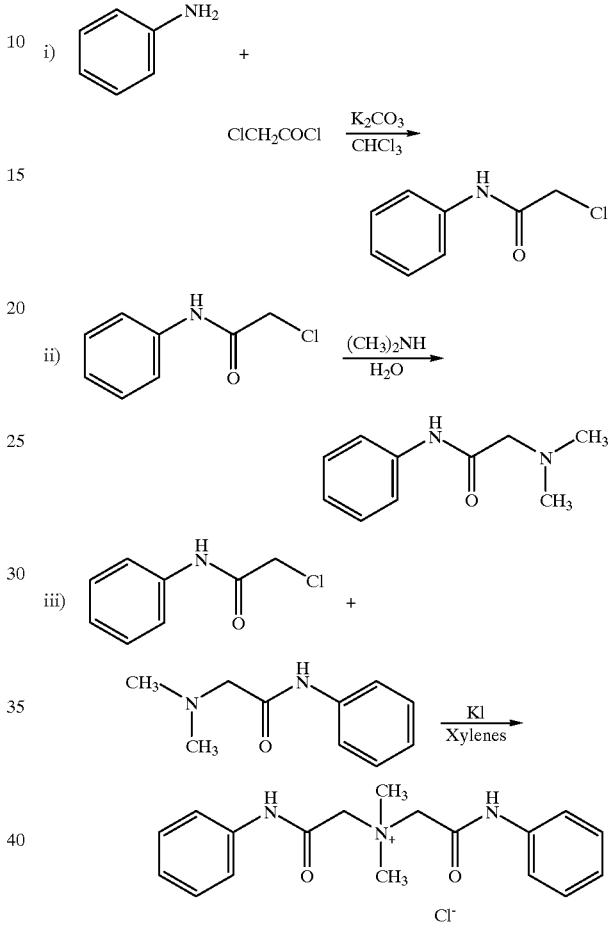

Another preferred compound of the present invention, N-(2,6-dimethylphenylcarbamoylmethyl) trimethylammonium chloride (Compound 2) is a compound of Formula I wherein R and $R_1$ are methyl; E is —CH$_2$—R$_2$ where R$_2$ is hydrogen; Y is

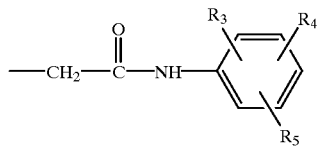

wherein $R_3$ is methyl at the C2 position of the phenyl ring, $R_5$ is methyl at the C6 position of the phenyl ring, $R_4$ is hydrogen and An$^{31}$ is the chloride anion. Compound 2 can be synthesized according to the reaction scheme shown below (see, e.g., T. Takahashi, J. Okada, M. Hori, A. Kato, K. Kanematsu and Y. Yamamoto, *J. Pharm. Sco. Japan,* 76, 1180–6 (1956), herein incorporated by reference) from commercially available starting materials and reagents (e.g., Aldrich Chemical Company, Milwaukee, Wis. and Sigma Chemical Company, St. Louis, Mo.):

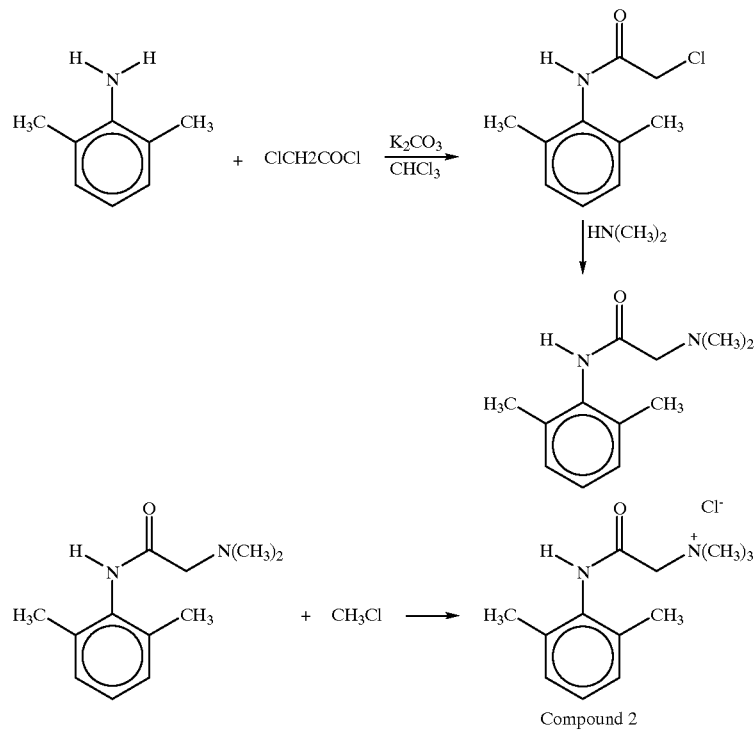

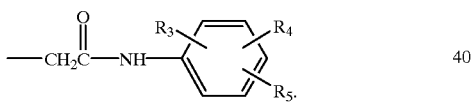

Compound 2

Another preferred compound of the present invention, N-(2,6-dimethylphenylcarbamoylmethyl) triethylammonium chloride (Compound 3) is a compound of Formula I wherein R and $R_1$ are ethyl; E is —$CH_2$—$R_2$ where $R_2$ is methyl; Y is

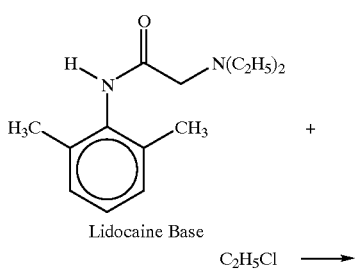

wherein $R_3$ is methyl at the C2 position of the phenyl ring, $R_5$ is methyl at the C6 position of the phenyl ring, $R_4$ is hydrogen and An⁻ is the chloride anion. Compound 3 can be synthesized by methods analogous to that described above for Compound 2. Alternatively, Compound 3 can be readily synthesized from lidocaine base (commercially available from Sigma Chemical Company, St. Louis, Mo.) in a simple reaction as shown below (G. K. Wang et al., Anesthesiology 83 1293–1301 (1995)):

-continued

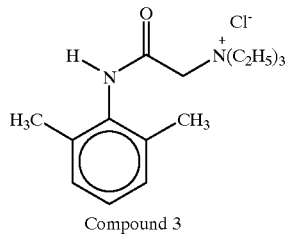

Compound 3

Other compounds encompassed by Formula I can be synthesized in an analogous manner and is within the skill in the art.

Suitable pharmaceutically acceptable salts include acid addition salts of acids such as hydrochloric, hydrobromic, benzenesulfonic (besylate), benzoic, camphorsulfonic, ethanesulfonic, fumaric, gluconic, glutamic, isethionic, maleic, malic, mandelic, methanesulfonic, mucic, nitric, pamoic, pantothenic, succinic, p-toluenesulfonic, phosphoric, sulphuric, citric, tartaric, lactic and acetic acid, although the preferred acid addition salt is the hydrochloride salt.

The magnitude of the therapeutic or prophylactic dose of the compounds of the present invention in the treatment and/or prevention of cough will depend upon the severity and nature of the condition being treated and the route of administration. The dose and the frequency of the dosing will also vary according to age, body weight and response of the individual patient. In general, the total daily dose range for the compounds of the present invention for the treatment and/or prevention of cough is from about 0.1 to about 800 mg in single or repeated doses.

Any suitable route of administration may be employed to provide an effective dosage of the compounds of the present invention, although administration by inhalation is preferred, most preferably in aerosol form. Suitable forms of administration include, but are not limited to, inhalation (delivered by, e.g., metered-dose inhaler, jet nebulizer, ultrasonic nebulizer, dry powder inhaler, etc.), nasal sprays, nebulization, oral administration such as via tablets, capsules, lozenges, syrups, sprays, suspensions, elixirs, gargles, and other liquid preparations, aerosol foams, parental administration, and sublingual administration.

The compounds of the present invention can include pharmaceutically acceptable carriers and other conventional additives, including aqueous based carriers, co-solvents such as ethyl alcohol, propylene glycol and glycerin, fillers, lubricants, wetting agents, flavoring agents, coloring agents, emulsifying, suspending or dispersing agents, suspending agents, etc. For aerosol delivery of the compounds of the present invention, pharmaceutically acceptable diluents, carriers, and/or propellants may be included in the formulations for use in appropriate devices. These are prepared by procedures well known to those skilled in the art (see e.g., Medication Teaching Manual, 5th Ed., Bethesda, Md., American Society of Hospital Pharmacists, 1991).

The compositions of the present invention may optionally include other known therapeutic agents, including decongestants such as pseudoephedrine HCl, phenylephrine HCl and ephedrine HCl, non-steroidal anti-inflammatory drugs such as acetaminophen, aspirin, phenacetin, ibuprofen and ketoprofen, expectorants such as glyceryl guaiacolate, terpin hydrate and ammonium chloride, antihistamines such as chlorpheniramine maleate, doxylamine succinate, brompheniramine maleate and diphenhydramine hydrochloride, and anesthetic compounds such as phenol.

The following examples are offered by way of illustration, and not by way of limitation:

EXAMPLE 1

Male albino Dunkin-Hartley strain guinea-pigs (weight 300–400 g) were supplied by Harlan UK Ltd., Bicester, Oxon, UK.

The method used was modified from that described by Adcock J. J., Schneider C. and Smith T. W., "Effects of Morphine and a Novel Opioid Pentapeptide BW443C, on Cough, Nociception and Ventilation in the Unanaesthetized Guinea-pig", Br. J. Pharmacol., 93, 93–100 (1988). Individual conscious guinea-pigs were placed unrestrained into a sealed purpose built perspex exposure chamber (3,000 cm$^3$ volume) and allowed to acclimatize prior to aerosol administration. The layout of the experimental apparatus used is shown in FIG. 1.

Cylinder air was introduced into the exposure chamber at a flow rate of 1 liter/min, maintained by a needle valve and monitored by a rotameter. From the rotameter the air passed through the cup of an ultrasonic nebulizer (DeVilbis UltraNeb 2000) which was used to generate aerosols of drug or citric acid at 0.15 ml/min. A Fleisch pneumotachograph, connected to a differential pressure transducer (Grass model PT5) was attached to the outflow from the exposure chamber and provided a measurement of airflow from the chamber. The differential pressure transducer was connected to a Grass polygraph from which a hard copy record was produced. The output from the polygraph was directed to a computerized data acquisition system (Poh-Ne-Mah) for real time recording of data. A tie-clip microphone was placed in the exposure chamber and connected via a preamplifier to a loudspeaker output to provide the observer with an audio monitor of responses.

Cough responses were induced by exposure to an aerosol of citric acid (1M) for 10 minutes. Animals were continuously monitored by trained observer, and the number of coughs were counted during a 15 minute period from commencement of the citric acid aerosol administration. Three characteristic responses were produced by exposure to citric acid: cough, sneeze and "wet dog" shake.

Figure 2A:
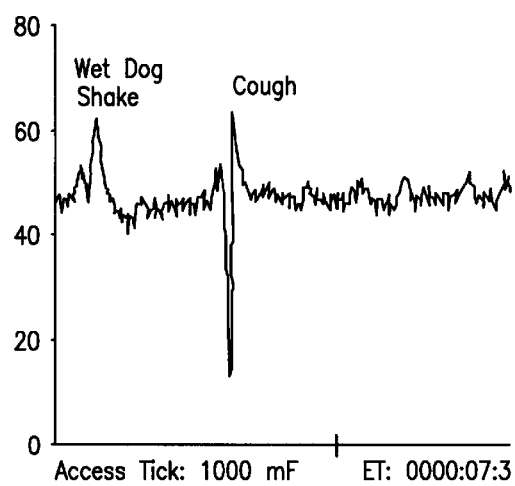
FIGS. 2A and 2B are expanded scale recordings of pressure changes derived from the differential pressure transducer during characteristic responses exhibited by a guinea-pig during exposure to an aerosol of citric acid.
Figure 2B:
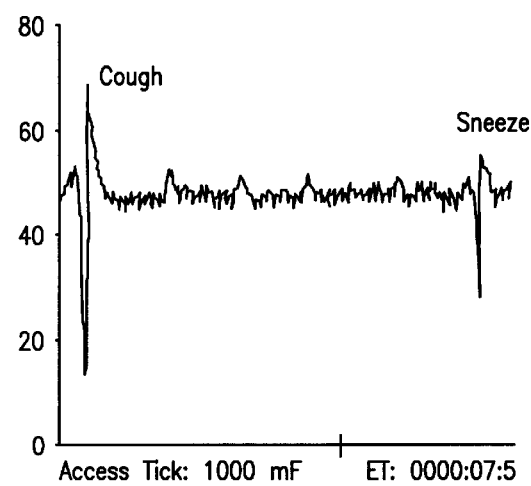

The three types of response were differentiated primarily by sound and visual observation. Confirmation of the numbers of multiple coughs was determined by reference to the change in flow rate displayed by the Poh-Ne-Mah system monitor. Printouts demonstrating the pressure changes characteristic of the different response to irritant are shown in FIGS. 2A and 2B. Data recorded for individual guinea-pigs on the Poh-Ne-Mah system was stored on an optical disk. Each cough was marked on the Grass polygraph paper trace, and from these record numbers, frequency and time of onset of coughs were determined. The cough response was defined by a characteristic coughing sound and behavior, associated with a marked biphasic pressure change. The biphasic pressure changes associated with a sneeze were not of as great a magnitude as those associated with a cough, the secondary rise in pressure also being far less than during a cough (FIG. 2B). The sound of a sneeze differed from that of a cough, and sneezing was associated with nose rubbing activity. The third response, a "wet dog" shake, produced a rise in pressure only (FIG. 2A) and lacked the definitive sound of a cough or sneeze.

Quantities of drugs were weighed out and dissolved in a vehicle. Equal volumes were aliquotted into sample tubes before being passed, together with another sample tube containing the same volume of vehicle, to an independent observer for coding. Pre-treatments were matched by concentration together with a vehicle control group. Five guinea-pigs were randomly allocated to each treatment group. Animals were pre-treated with either vehicle (0.9% sterile saline), lidocaine or test drugs for 5 minutes immediately prior to citric acid aerosol exposure. Test drugs and lidocaine were administered as aerosols at concentrations of 0.1, 1.0 and 10.0 mg/ml. The sequence of pre-treatment administration was determined according to a 4×4 Latin Square design.

Data presented as the mean ±SEM number of coughs produced by individual guinea-pigs within each group during the 15 minute observation period or mean±SEM latency of cough were analyzed using one way analysis of variance to compare mean responses between matched groups of animals (doses) and between unmatched groups (treatments) followed by the Tukey-Kramer multiple comparison test where appropriate.

Results

Data from one animal (number 1) in group B (vehicle control for 10 mg/ml doses) was excluded because the animal was exposed to an insufficient aerosol of citric acid.

The time course of cough responses to citric acid aerosol in vehicle treated guinea-pigs was recorded. A latent period of approximately 60 seconds passed between the start of the citric acid aerosol and the first cough (Table 1). Thereafter, the frequency of coughs increased, reaching a peak at between 2–3 minutes before gradually reducing over the subsequent 7–8 minutes. At 10 minutes. the citric acid aerosol was stopped and the number of coughs observed trailed off to zero at between 14–15 minutes. There was no difference in the mean number of coughs produced by the three groups of vehicle pre-treated animals in the 15 minutes following citric acid aerosol exposure (Table 2).

TABLE 1

Mean latency of Cough
Time (seconds) to onset of first cough after initiation of
citric acid aerosol

| Aerosol Conc. | Saline | Lidocaine | Compound 1 |
|---|---|---|---|
| 0.1 mg/ml | 58 ± 14 | 88 ± 20 | 88 ± 6* |
| 1.0 mg/ml | 94 ± 19 | 92 ± 25 | 103 ± 11* |
| 10 mg/ml | ᵃ56 ± 18 | 136 ± 21 | 778 ± 137⁻ |

Values are mean ± SEM for n = 5 or ᵃn = 4 guinea-pigs per group.
*P < 0.001 compared to 10 mg/ml;
⁻P < 0.001 compared to saline and lidocaine (ANOVA followed by Tukey-Kramer multiple comparisons test).

TABLE 2

Total Coughs
Number of coughs produced by an aerosol of 1M citric acid
administered for 10 min. Coughs were counted over the 15 min
period following initiation of citric acid aerosol.
Percentage reduction of the cough response compared with matched
vehicle control groups is shown by the values in parentheses.

| Aerosol Conc. | Saline | Lidocaine | Compound 1 |
|---|---|---|---|
| 0.1 mg/ml | 30.0 ± 6.9 | 27.2 ± 5.3 (9.3%) | 22.4 ± 6.0* (25.3%) |
| 1.0 mg/ml | 28.2 ± 6.0 | 19.0 ± 4.3 (32.6%) | 16.8 ± 4.0** (40.4%) |
| 10 mg/ml | ᵃ28.8 ± 6.5 | 15.0 ± 3.0 (40.9%) | 0.6 ± 0.6⁻ (97.6%) |

Values are mean ± SEM for n = 5 or ᵃn = 4 guinea-pigs per group.
**P < 0.05 and *P < 0.01 compared to 10 mg/ml;
⁻P < 0.05 compared to lidocaine and P < 0.001 compared to saline (ANOVA followed by Tukey-Kramer multiple comparisons test).

Lidocaine pre-treatment had no significant effect on the time course of cough responses at any of the concentrations used, but did appear to delay onset of the first cough at 10 mg/ml (Table 1) and reduce cough frequency at both 1.0 and 10 mg/ml.

Compound 1 prolonged the latency of cough onset at 10 mg/ml (Table 1). Pre-treatment of guinea-pigs with Compound 1 produced a concentration related reduction of the total number of coughs induced by citric acid over the 15 minute observation period (Table 2) which was highly significant compared with both the matched vehicle group and the matched lidocaine group at 10 mg/ml. The percentage reduction compared with matched vehicle treated guinea-pigs is shown in Table 2. The frequency of coughs was reduced at 1 mg/ml. At the higher concentration of 10 mg/ml, cough responses were completely inhibited in 4 of the 5 guinea-pigs in the group, producing a significant prolongation of the latency of cough (Table 1).

With Compound 1 at 10 mg/ml, in those animals that did not cough (4 of 5) there was a marked absence of sneezing.

EXAMPLE 2

In another experiment similar to that described above in Example 1, the anti-tussive activity of N-(2-6-dimethylphenylcarbamoylmethyl) trimethylammonium chloride (Compound 2) and N-(2,6-dimethylphenylcarbamoylmethyl) triethylammonium chloride (Compound 3) were tested. Results showed that both Compound 2 and Compound 3 are effective.

Pre-treatment of guinea pigs with aerosols of Compound 2 immediately before exposure to citric acid inhibited cough responses by over 80% compared with matched vehicle pre-treated guinea pigs.

Pre-treatment of guinea pigs with aerosols of Compound 3 immediately before exposure to citric acid inhibited cough responses by over 70% compared with matched vehicle pre-treated guinea pigs.

EXAMPLE 3

The duration of the anti-tussive effects of Compound 1 and lidocaine against citric acid-induced cough responses were investigated in conscious guinea pigs. Test agents or vehicle were administered as aerosol pre-treatments (10 mg/ml, 5 minute duration) at 5 minutes, 30 minutes, 1 hour, 2 hours and 4 hours prior to induction of cough responses by citric acid aerosol.

Pre-treatment of guinea pigs with aerosols of Compound 1 immediately before exposure to citric acid inhibited cough responses by 84.9% compared with matched vehicle pre-treated guinea pigs.

Aerosolized Compound 1 remained an effective antitussive pre-treatment when administered between 30 minutes and 2 hours before induction of cough responses with citric acid, significantly inhibiting responses by 63% after 30 minutes, 60.7% after 60 minutes and by 44.0% after 2 hours.

Increasing the period of time between pre-treatment with Compound 1 and citric acid exposure to 4 hours resulted in a modest 15% reduction in mean number of citric acid-induced cough responses.

The time to the first recorded cough response elicited by citric acid was prolonged by Compound 1 pre-treatment immediately prior to citric acid exposure, when latency of cough onset increased 3.3. fold.

Pre-treatment of guinea pigs with aerosols of lidocaine did not result in a significant inhibition of cough responses compared with matched vehicle pre-treated guinea pigs at any of the time points. None of the lidocaine pre-treatments affected the latency of cough onset.

EXAMPLE 4

The antitussive effects of a 5 minute pre-treatment with aerosolized Compound 1 and lidocaine on capsaicin aerosol-induced cough were investigated in conscious guinea pigs.

Pre-treatment of guinea pigs with aerosols of lidocaine at 10 and 30 mg/ml reduced the number of capsaicin-induced cough responses by 42.2% and 10.3% respectively compared with matched vehicle pre-treated guinea pigs, but this effect was not significant (P>0.05).

Pre-treatment of guinea pigs with aerosols of Compound 1 at 10 and 30 mg/ml reduced the number of capsaicin-induced cough responses by 25% (P>0.05) and 76.9% (P<0.01) respectively, compared with matched vehicle treated guinea pigs.

Lidocaine had little effect on the mean latency of cough onset at either 10 or 30 mg/ml, producing only changes of 1.2 and 0.8 fold, respectively.

At a concentration of 10 ml/ml, Compound 1 had no significant effect on latency of cough onset. However, pre-treatment with a higher dose of Compound 1 (30 mg/ml) prolonged the mean latency of cough onset by 2.1 fold (P<0.05).

EXAMPLE 5

The antitussive effects of Compound 1 and lidocaine administered after induction of cough responses by exposure to citric acid aerosol were investigated in conscious guinea pigs. Vehicle or test agents were administered as aerosols (10 mg/ml; 5 minute duration) 2 minutes after exposure to citric acid aerosol began. Cough responses were recorded during a 15 minute observation period (t=0 to t=15 min.) from initiation of citric acid exposure.

Therapeutic treatment of guinea pigs with aerosols of Compound 1 during exposure to aerosolized citric acid inhibited the total number of cough responses recorded during the 15 minute observation period by 63.8% ($P<0.001$) compared with matched vehicle treated guinea pigs.

In contrast, total cough responses in guinea pigs treated therapeutically with aerosols of lidocaine were reduced by only 32.4% (n.s.) of that recorded for the matched vehicle treated guinea pigs.

Further analysis of the number of cough responses revealed that between t=2 and t=10 minutes, Compound 1 and lidocaine significantly reduced the number of cough responses, inhibiting coughs by 70.8% ($P<0.001$) and 39.1% ($P<0.05$), respectively.

EXAMPLE 6

Investigation of Antitussive Activity of Aerosolized Compound 1 on Citric Acid-induced Cough Responses in Conscious Rabbits Protocol Twenty-two male New Zealand white rabbits were randomly allocated to either of two groups of 11 rabbits.

Pairs of rabbits (control versus test) were placed in individual exposure chambers with an airflow of 5 liter/min through the chambers.

Each rabbit was exposed to ozone (3 ppm) for 1 hour.

The rabbits were then immediately exposed to aerosols of either vehicle (chamber 1) or Compound 1 (10 mg/ml, chamber 2) at a nebulization rate of 0.9 ml/min.

Cough responses were induced with citric acid aerosol (1.6 M).

Coughs were counted during the 10 minute exposure to citric acid.

Results

All rabbits were exposed to ozone before vehicle or test drug pre-treatment. The mean ±SEM number of citric acid-induced cough responses recorded in vehicle pre-treated rabbits was 22.0±5.1. This level of response was significantly reduced to 2.7±0.9 coughs in Compound 1 pre-treated rabbits (P=0.004, unpaired t test).

All publications and patent applications mentioned in this specification are herein incorporated by reference to the same extent as if each individual publication or patent application was specifically and individually incorporated by reference.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for the treatment and/or prevention of cough in warm-blooded animals, which method comprises administering to a warm-blooded animal in need thereof a therapeutically effective amount of a compound of formula I as set forth below:

(I)

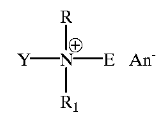

wherein R and $R_1$ are independently selected from $C_1$–$C_8$ alkyl, $C_3$–$C_8$ alkoxyalkyl and $C_7$–$C_{12}$ aralkyl; Y and E are independently selected from —$CH_2$—$R_2$ or:

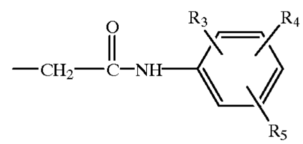

wherein $R_2$ is independently selected from hydrogen, $C_1$–$C_8$ alkyl, $C_3$–$C_8$ alkoxyalkyl and $C_7$–$C_{12}$ aralkyl; and where $R_3$, $R_4$ and $R_5$ are independently selected from bromine, chlorine, fluorine, carboxy, hydrogen, hydroxy, hydroxymethyl, methanesulfonamido, nitro, sulfamyl, trifluoromethyl, $C_2$–$C_7$ alkanoyloxy, $C_1$–$C_6$ alkyl, $C_1$–$C_6$ alkoxy, $C_2$–$C_7$ alkoxycarbonyl, $C_1$–$C_6$ thioalkyl, aryl and $N(R_6,R_7)$ where $R_6$ and $R_7$ are independently selected from hydrogen, acetyl, methanesulfonyl and $C_1$–$C_6$ alkyl, $An^-$ is an anion of an acid addition salt of a pharmaceutically acceptable acid or an anion from a pharmaceutically acceptable salt; and isolated enantiomeric, diastereomeric and geometric isomers thereof, and mixtures thereof, together with one or more pharmaceutically acceptable carriers, with the proviso that Y and E cannot both be —$CH_2$—$R_2$ in the same compound.

2. A method for the treatment and/or prevention of cough in warm-blooded animals, which method comprises administering to a warm-blooded animal in need thereof a therapeutically effective amount of N,N-bis (phenylcarbamoylmethyl)dimethylammonium chloride.

* * * * *